United States Patent [19]

Baldwin et al.

[11] Patent Number: 5,276,025
[45] Date of Patent: Jan. 4, 1994

[54] HETEROBICYCLIC SULFONAMIDES

[75] Inventors: John J. Baldwin, Gwynedd Valley; Jacob M. Hoffman, Jr., Lansdale; James H. Jones, Fort Washington; Clarence S. Rooney, Worcester; Anthony M. Smith, Telford, all of Pa.

[73] Assignee: Merck & Co., Inc., Rahway, N.J.

[21] Appl. No.: 942,652

[22] Filed: Sep. 9, 1992

[51] Int. Cl.$^5$ .................... A61K 31/55; C07D 495/04
[52] U.S. Cl. .................................... 514/211; 540/552; 540/490; 549/64
[58] Field of Search .................... 540/552; 514/211

[56] References Cited

U.S. PATENT DOCUMENTS 4,619,939 10/1986 Maren ........................... 514/363

FOREIGN PATENT DOCUMENTS 452151 10/1991 European Pat. Off.
91/15486 10/1991 World Int. Prop. O.

OTHER PUBLICATIONS

Lippa et al., Arch Ophthalmol., vol. 110, vol. 110; pp. 495-499; 1992.
Abstract: 1369: Lippa et al., Assoc. For Research and Vision in Ophthalmology. 1991.
Abstract: 1576: McMahon et al., Assoc for Research and Vision in Ophthalmology. 1991.
Abstract: 1577: Cyrlin et al., Assoc. for Research and Vision in Ophthalmology. 1991.
Abstract; 1578: Kass et al., Assoc. for Research and Vision in Ophthalmology. 1991.
Abstract: 1579: Mardin et al., Assoc. for Research and Vision in Ophthalmology. 1991.
Abstract; 3064: Lesure et al., Assoc for Research and Vision in Ophthalmology. 1991.
Lippa et al., Ophthalmology, vol. 98, No. 3 pp. 308-313; 1991.
Unnumbered Abstract: Hofmann et al. Glaucoma Symposium of International Congress of Ophthalmology, 1990.
Abstract: 1148-44, Bourgeois et al., Assoc. for Research and Vision in Ophthalmology, 1990.
Unnumbered Abstract: Lippa et al., Glaucoma Symposium of International Congress of Ophthalmology. 1990.
Unnumbered Abstract: Gervasoni et al., Amer. Soc. of Clinical Pharmacology and Therapeutics. 1991.

*Primary Examiner*—Mark L. Berch
*Assistant Examiner*—P. K. Sripada
*Attorney, Agent, or Firm*—Sylvia A. Ayler; Mark R. Daniel

[57] ABSTRACT

Compounds of general formula:

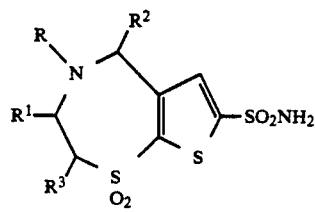

are topically effective carbonic anhydrase inhibitors useful in the treatment of ocular hypertension and related disorders such as glaucoma.

6 Claims, No Drawings

HETEROBICYCLIC SULFONAMIDES

SUMMARY OF THE INVENTION

This invention is concerned with novel heterobicyclic sulfonamides of structural formula

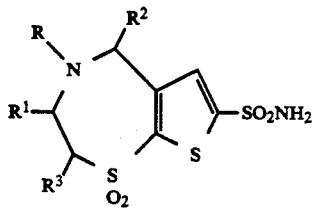

and the ophthalmologically acceptable salts thereof which are useful for treating ocular hypertension and glaucoma.

The invention is also concerned with novel ophthalmological formulations comprising one of the novel compounds as the sole active ingredient or in combination with other active ingredients.

The invention is also concerned with a novel method of treating ocular hypertension and glaucoma by topical administration of one of the novel compounds or formulation thereof to a hypertensive eye.

BACKGROUND OF THE INVENTION

Glaucoma is an ocular disorder associated with elevated intraocular pressures which are too high for normal function and may result in irreversible loss of visual function. If untreated, glaucoma may eventually lead to blindness. Ocular hypertension, i.e., the condition of elevated intraocular pressure without optic nerve head damage or characteristic glaucomatous visual field defects, is now believed by many ophthalmologists to represent the earliest phase of glaucoma.

Many of the drugs currently used to treat glaucoma proved not entirely satisfactory. Indeed, few advances were made in the treatment of glaucoma since pilocarpine and physostigmine were introduced until β-adrenergic blocking agents were found effective in reducing intraocular pressure. While many of these agents are effective in reducing intraocular pressure, they also have other characteristics, e.g. membrane stabilizing activity, that are not acceptable for chronic ocular use. (S)-1-tert-Butylamino-[(4-morpholino-1,2,5-thiadiazol-3-yl)oxy]-2-propanol, a β-adrenergic blocking agent, was found to reduce intraocular pressure and to be devoid of many unwanted side effects associated with pilocarpine and, in addition, to possess advantages over many other β-adrenergic blocking agents, e.g. to be devoid of local anesthetic properties, and to have a long duration of actions.

Although pilocarpine, physostigmine and the β-blocking agents mentioned above reduce intraocular pressure, none of these drugs manifests its action by inhibiting the enzyme carbonic anhydrase and, thereby, impeding the contribution to aqueous humor formation made by the carbonic anhydrase pathway.

Agents referred to as carbonic anhydrase inhibitors block or impede this inflow pathway by inhibiting the enzyme, carbonic anhydrase. While such carbonic anhydrase inhibitors are now used to treat intraocular pressure by oral, intravenous or other systemic routes, they thereby have the distinct disadvantage of inhibiting carbonic anhydrase throughout the entire body. Such a gross disruption of a basic enzyme system is justified only during an acute attack of alarmingly elevated intraocular pressure, or when no other agent is effective. Despite the desirability of directing the carbonic anhydrase inhibitor only to the desired ophthalmic target tissue, no topically effective carbonic anhydrase inhibitors are available in the pharmacies for clinical use.

However, related topically effective carbonic anhydrase inhibitors are reported in U.S. Pat. Nos. 4,677,115 and 4,797,413.

DETAILED DESCRIPTION OF THE INVENTION

The novel compound of this invention has structural formula I:

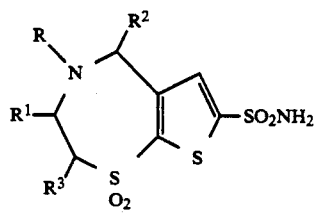

or the individual enantiomers, mixtures of the enantiomers, or an ophthalmologically acceptable salt of the compound, or its enantiomers, wherein: R, $R^1$ and $R^2$ are independently hydrogen, $C_{1-5}$ alkyl or $C_{3-6}$ cycloalkyl; and $R^3$ is hydrogen, $C_{1-5}$ alkyl either unsubstituted or substituted with $C_{1-3}$ alkoxy, $C_{1-3}$ alkoxy-$C_{1-3}$ alkoxy, hydroxy, hydroxy-$C_{1-3}$ alkoxy or $N(R^4)_2$ wherein the $R^4$ groups are the same or different and are hydrogen or $C_{1-3}$ alkyl.

One embodiment of the novel compounds is that wherein $R^2$ is hydrogen.

A class of compounds within this embodiment is that wherein R and $R^1$ are hydrogen or $C_{1-5}$ alkyl and $R^3$ is hydrogen, $C_{1-5}$ alkyl or $C_{1-3}$ alkoxy-$C_{1-5}$ alkyl.

Also included within the scope of the present invention are the non-toxic pharmaceutically acceptable salts of the novel compounds. Acid addition salts are formed by mixing a solution of those members of Compound I having a basic nitrogen atom with a solution of a pharmaceutically acceptable non-toxic acid such as hydrochloric acid, fumaricacid, isethionic acid, lactic acid, maleic acid, succinic acid, acetic acid, citric acid, tartaric acid, phosphoric acid, or the like.

Also included within the scope of this invention are diastereomers and enantiomers of the novel compounds and mixtures thereof.

The novel pharmaceutical formulations of this invention are adapted for topical ocular administration in the form of solutions, ointments, solid water soluble polymeric inserts, or gels.

The novel ophthalmological formulations of this invention contain about 0.1% to 15% by weight of medicament, especially about 0.5 to 4% by weight of medicament, the remainder being comprised of carriers and other excipients well known in the art for ophthalmological preparations.

The medicament in the novel topical ocular formulation is one of the novel compounds of this invention either alone or in combination with a β-adrenergic blocking agent such as timolol maleate or a parasympathomimetic agent such as pilocarpine. In such combinations the two active agents are present in approximately equal amounts.

The novel method of treatment of this invention comprises the treatment of elevated intraocular pressure by topical ocular administration of about 0.1 to 25 mg and especially 0.2 to 10 mg of novel compound per day, either by single dose or on a 2 to 4 dose per day regimen.

The novel compounds of this invention are prepared in accordance with the following synthetic Schemes and discussion produces the 3-carboxy derivative 3. The sulfonamide group is introduced to produce 4 by treatment of 3 with chlorosulfonic acid at about $-5°$ C. followed by isolation of the sulfonyl chloride and portion wise addition of it to a mixture of ice/water/$NH_4OH$/acetone. The carboxyl group of 4 is esterified to produce 5 with ethanol or other lower alkanol in the presence of a catalytic amount of sulfuric acid. Cyclization to 6 is accomplished by adding 2-aminoethanethiol to a solution of sodium in ethanol followed by the addition of 5. Oxidation to the sulfone 7, occurs on treatment of 6 with Oxone in aqueous methanol at about $80°$ C.

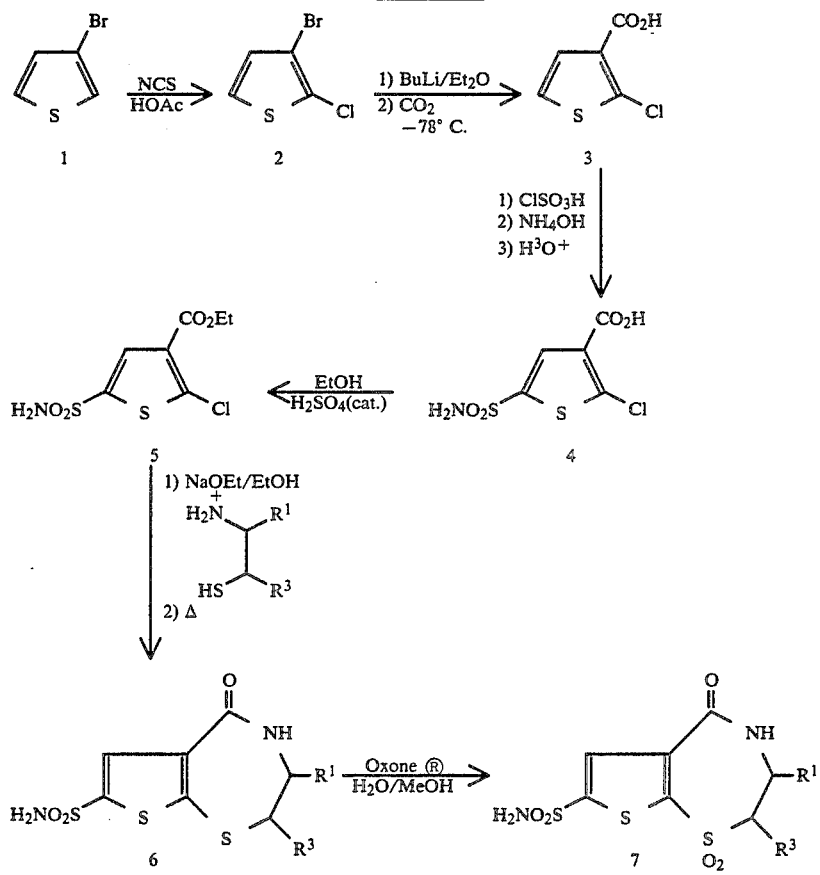

SCHEME I

| | Abbreviations |
|---|---|
| Ac | acetic |
| Bu | n-butyl |
| DMF | dimethyl formamide |
| Et | ethyl |
| Im | imidazole |
| Me | methyl |
| NCS | N-chlorosuccinimide |
| THF | tetrahydrofuran |

Synthetic Scheme I shows the synthetic route to the key intermediate 7. Bromothiophene 1 is chlorinated with N-chlorosuccinimide in refluxing acetic acid solution to give 2. Treatment of 2 in ether with n-butyllithium at $-78°$ C. followed by rapid addition of $CO_2$ In synthetic Scheme II there is shown, the reduction of the oxo group in 7 to 8 with borane. THF complex in refluxing THF. The nitrogen of 8 can then be substituted by acylation to give 9 or by direct alkylation to give 11. The acylation is performed with an acid anhydride or chloride in the presence of a strong base such as triethylamine or diisopropylethylamine. The resulting carbonyl of the N-acyl group of 9 may be reduced to methylene with borane-dimethylsulfide complex in refluxing THF. A Lewis acid, such as boron trifluoride, may be added to facilitate the reduction. Direct alkylation of 8 to 11 is conducted with an alkyl halide, such as the iodide or bromide in the presence of triethylamine in DMF.

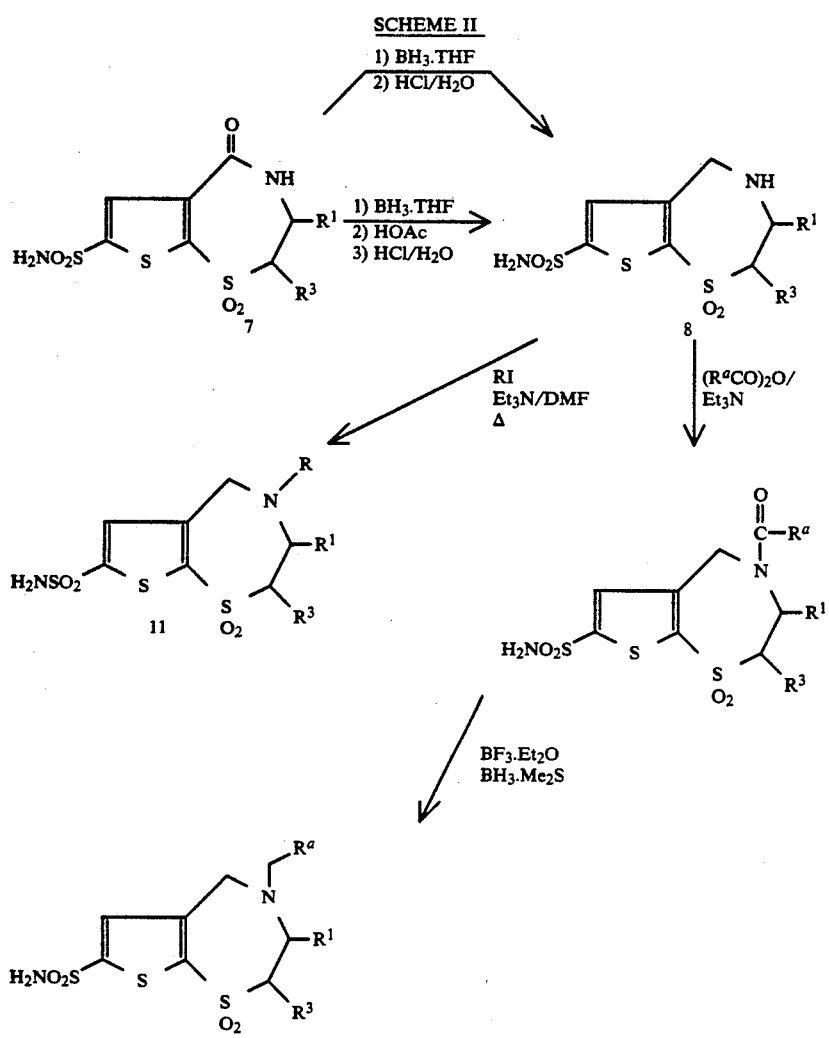

Synthetic Scheme III is useful for positioning a substituent at position 5 of the ring system. Treatment of 5 with 1,1-carbonyldiimidazole in DMF followed by treatment with N,O-dimethylhydroxylamine hydrochloride provides 12. Treatment of 12 with an alkyllithium $R^bLi$, such as methyllithium in THF at −78° C. yields the 3-acylthiophene 13 which on treatment with sodium ethoxide and aminoethanethiol as in Scheme I (5→6) provides an intermediate imine which is reduced with sodium borohydride in ethanol to give 14. Oxidation to the sulfone 16 and substitution on the nitrogen is accomplished as previously described in Reaction Scheme II to give 18.

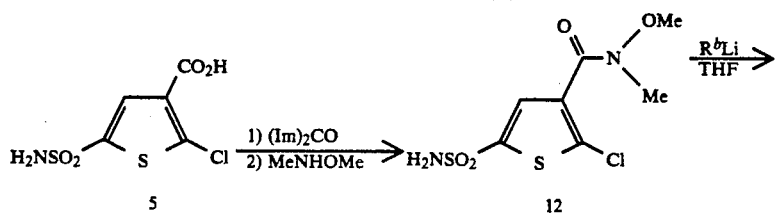

SCHEME III

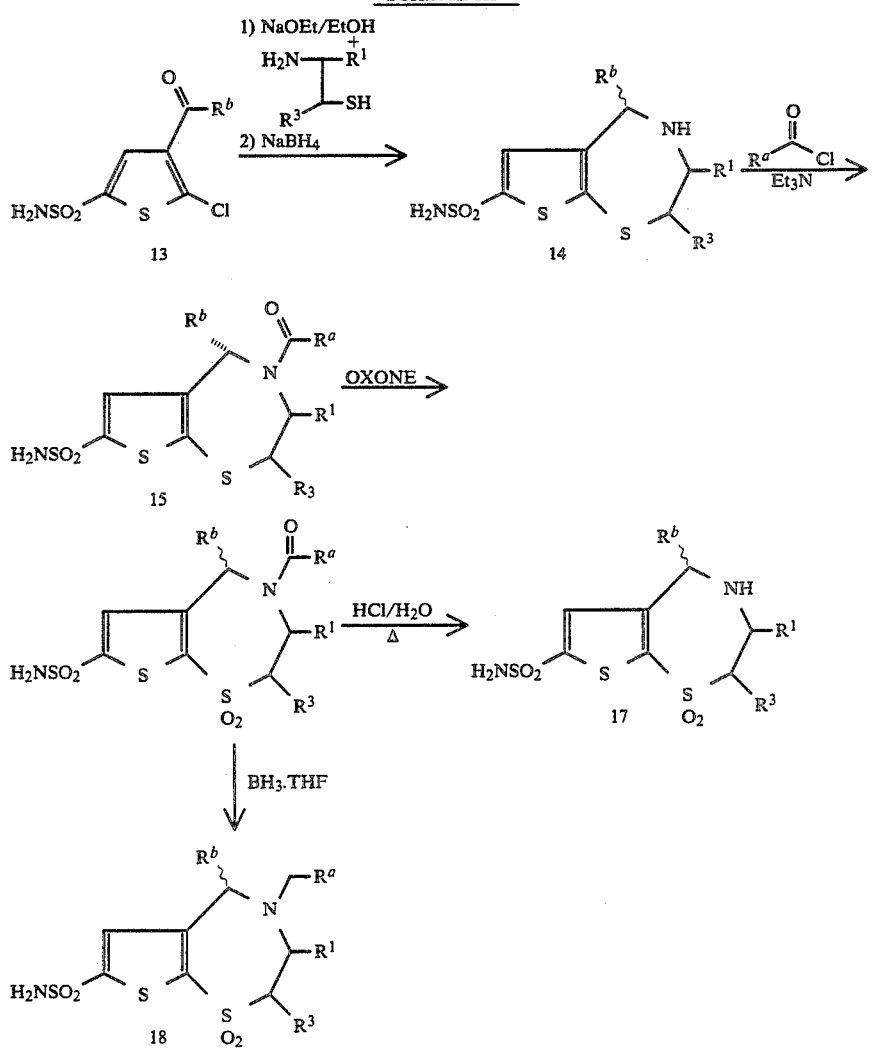

wherein $R^b$ is $C_{1-4}$alkyl

Treatment of BOC-protected 18 with excess butyllithium in THF at −78° C. followed by the addition of an alkyl halide or a substituted alkyl halide ($R^3$ halide) and removal of the BOC group with acid provides the 7-$R^3$ derivative 19 in Scheme IV.

Using ethylene oxide in place of an alkyl halide provides the 7-hydroxyethyl derivative 20. This in turn is converted to the tosylate or mesylate in pyridine with tosyl chloride or mesyl chloride respectively which is readily converted to the 7-aminoethyl 21 or 7-alkoxyethyl 22 derivative with an amine or an alcohol respectively.

SCHEME IV

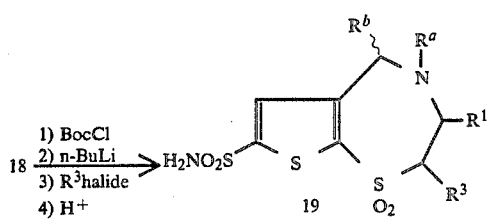

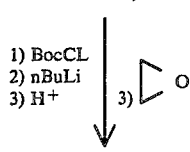

SCHEME IV -continued

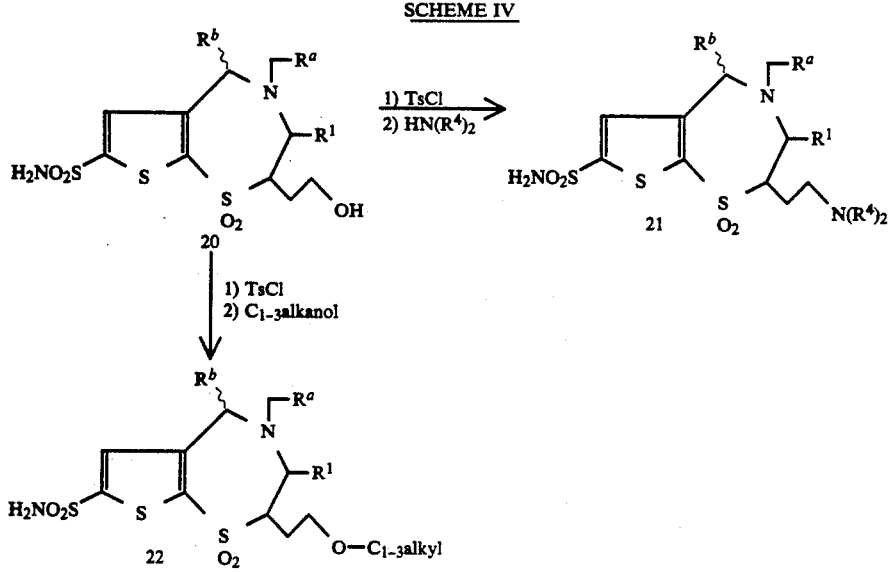

EXAMPLE 1

7-Sulfamoyl-2,3,4,5-tetrahydrothieno[3,2-f]-1,4-thiazepine-1,1-dioxide hydrochloride

Step A: Preparation of 2-chloro-3-bromothiophene

To a round bottomed flask were added glacial acetic acid (115.0 mL) along with 3-bromothiophene (25.0 g, 153.3 mmole). The reaction mixture was heated to reflux and N-chlorosuccinimide (20.58 g, 154.0 mmole) was added portion-wise (Note: reaction vigorous upon each addition!). After the addition was complete the reaction mixture was refluxed for three additional hours. The reaction mixture was cooled, poured onto ice/water and extracted (ethyl acetate). The combined extracts were washed with water, dilute HCl, and brine. Solvent removal yielded 27.91 g (87%) of a dark liquid. The sample was distilled before further use.

Step B: Preparation of 2-chlorothiophene-3-carboxylic acid

To a round bottomed flask were added 2-chloro-3-bromothiophene (26.2 g, 132.7 mmole) along with diethyl ether (390 mL). The reaction was cooled to $-78°$ C. (dry ice/acetone) and 1.6M n-butyllithium (87.0 mL, 139.0 mmole) was added dropwise. The reaction was stirred for 1.5 hours after which an excess of $CO_2$ (~25.0 g) was added all at once. The reaction was warmed to room temperature and poured onto ice/water. The mixture was extracted with 10% sodium carbonate solution and the basic aqueous layer was washed with methylene chloride. The basic solution was then acidified to a pH 3.0 and extracted with diethyl ether. The organic layer was washed with water, brine, and dried ($MgSO_4$). Solvent removal yielded 19.32 g of an off-white solid (90%) which was used as is.

$^1$H NMR($CDCl_3$) δ: 7.11 (d, 1H), 7.42 (d, 1H).

Step C: Preparation of 5-chloro-4-carboxythiophenesulfonamide

To a round bottomed flask was added chlorosulfonic acid (30 mL). The flask was then cooled to ~5° C. using ice/acetone. To this was added 2-chlorothiophene-3-carboxylic acid (5.0 g, 30.8 mmole) portion-wise. The reaction mixture was allowed to warm to room temperature and then heated to 85° C. for 1.75 hrs. The reaction mixture was cooled to room temperature and slowly poured onto ice/water. The solid that formed was collected and dried to yield 7.29 g (91%) of the crude sulfonyl chloride. The sulfonyl chloride was added portion-wise to a mixture of ice/water/$NH_4OH$/acetone. After the addition the reaction was allowed to warm to room temperature and the solvents were partially removed under vacuum. The resulting basic aqueous layer was then acidified (conc HCl) and the precipitated solid was dried yielding 4.98 g (67%) of material mp=224° C. (dec.).

$^1$H NMR ($CDCl_3$) δ: 8.18 (s, 1H).

Anal. calcd for $C_5H_4ClNO_4S_2$: C, 24.85; H, 1.67; N, 5.80. Found: C, 24.59; H, 1.85; N, 6.02.

Step D: Preparation of 5-chloro-4-carboethoxythiophene-2-sulfonamide

To a round bottom flask were added 5-chloro-4-carboxythiophene-2-sulfonamide (5.0 g, 20.7 mmole) along with toluene (25 mL), ethanol (20 ml), and conc. $H_2SO_4$ (25 drops). The reaction mixture was refluxed for 96 hours. The reaction mixture was cooled and the solvent was removed under vacuum. The residue was then poured onto ice and the pH adjusted to ~8.0 using 10% sodium carbonate. The basic aqueous layer was extracted with ethyl acetate and the organic layer was washed with water, brine, and dried ($MgSO_4$). Solvent removal yielded 3.92 g (70%) of an off white solid which was used as is: mp =98°-99° C.

$^1$H NMR ($d_6$-Acetone) δ: 1.36 (t, 3H, J-Hz), 4.36 (q, 2H, J-Hz), 7.78 (s, 1H).

Step E: Preparation of 7-sulfamoyl-3,4-dihydrothieno[3,2-f]-1,4-thiazepin-5(2H)-one To a round bottomed flask were added ethanol (200 mL) followed by solid sodium (1.0 g, 43.5 mmole). After the sodium dissolved, 2-aminoethanethiol was added (1.57 g, 20.4 mmole). The reaction was stirred for approximately 5.0 minutes and 5-chloro-4-carboethoxythiophene-2-sulfonamide (5.0 g, 18.5 mmole) was added.

The reaction was heated at reflux for 24 hrs. The cooled reaction mixture was acidified (6.0N HCl) and the solvent was removed under vacuum. The residue was triturated with water and the resulting solid collected: 4.77 g (98%) mp>270° C.

$^1$H NMR (d$_6$-DMSO) δ: 3.30–3.29 (m, 4H), 7.57 (s, 1H), 7.82 (s, H2NSO2—), 7.42 (t, —NH—).

Anal. calcd for C$_7$H$_8$N$_2$O$_3$S$_3$: C, 31.80; H, 3.05; N, 10.60. Found: C, 32.03; H, 3.25; N, 10.26.

Step F: Preparation of 7-sulfamoyl-3,4-dihydrothieno[3,2-f]-1,4-thiazepin-5(2H)-one-1,1-dioxide To a round bottomed flask were added 7-sulfamoyl-3,4-dihydrothieno[3,2-f]-1,4-thiazepin-5(2H)-one (830 mg, 3.1 mmole) along with methanol (50 mL), water (20 mL), and Oxone® (2.89 g, 4.7 mmole). The reaction mixture was warmed at 80° C. for one hour. The solvent was partially removed and additional water added. This yielded 700 mg (75%) of a white solid.

$^1$H NMR (d$_6$-DMSO) δ: 3.61 (q, 2H), 3.90 (t, 2H), 7.48 (s, H), 8.15 (s, H$_2$NSO$_2$—), 8.64 (t, NH),

Anal. calcd for C$_7$H$_8$N$_2$O$_5$S$_3$: C, 28.37; H, 2.72; N, 9.46. Found: C, 28.56; H, 2.83; N, 9.47.

Step G: Preparation of 7-sulfamoyl-2,3,4,5-tetrahydrothieno[3,2-f]-1,4-thiazepin-1,1-dioxide hydrochloride To a round bottomed flask were added THF (250 mL) along with 7-sulfamoyl-3,4-dihydrothieno-[3,2-f]-1,4-thiazepin-5(2H)-one-1,1-dioxide (4.58 g, 15.5 mmole). To this suspension was added BH$_3$•THF (75 mL, 75 mmole) portion-wise. The reaction mixture was heated at reflux for 5.0 hrs, cooled and allowed to stir overnight at room temperature. The reaction was quenched with acetic acid (6.0 mL) followed by 6.0N HCl (15 mL). A precipitate formed and was collected yielding 5.4 g of a solid. The solid material was dissolved in water and washed with ethyl acetate. The solution was then basified and washed with ethyl acetate. The basic solution was cooled in ice/water and acidified (HCl) yielding 2.47 g (50%) of a solid. Recrystallization from ethyl acetate/methanol yielded 1.75 g of material mp=250° C. dec.

$^1$H NMR (d$_6$-DMSO) δ: 3.43 (m, 2H), 3.58 (m, 2H), 4.06 (s, 2H), 7.6 (s, 1H), 8.03 (s, H$_2$NSO$_2$—).

Anal. calcd for C$_7$H$_{10}$N$_2$O$_4$S$_3$•HCl: C, 26.37; H, 3.48; N, 8.79. Found: C, 26.28; H, 3.56; H, 8.72.

EXAMPLE

4-Ethyl-7-sulfamoyl-2,3,4,5-tetrahydrothieno-[3,2-f]-1,4-thiazepin-1,1-dioxide hydrochloride

Step A: Preparation of 4-acetyl-7-sulfamoyl-2,3,4,5-tetrahydrothieno[3,2-f]-1,4-thiazepine-1,1-dioxide A solution of 7-sulfamoyl-2,3,4,5-tetrahydrothieno[3,2-f]-1,4-thiazepin-1,1-dioxide (240 mg, 0.85 mmole) in acetonitrile (5 mL) and tetrahydrofuran (5 mL) containing acetic anhydride (100 mg, 0.94 mmol) and triethylamine (0.17 mL, 1.22 mmol) was stirred at ambient temperature for 1.5 hours. The solvents were evaporated and the residue chromatographed on silica gel. Elution with 10% methanol-methylene chloride gave 250 mg (77%) of the title compound. This material was used as is.

Step B: Preparation of 4-ethyl-7-sulfamoyl-2,3,4,5-tetrahydrothieno[3,2-f]-1,4-thiazepin-1,1-dioxide hydrochloride 4-Acetyl-7-sulfamoyl-2,3,4,5-tetrahydrothieno[3,2-f]-1,4-thiazepin-1,1-dioxide (200 mg, 0.62 mmol) was dissolved in dry THF (10 mL), boron trifluoride etherate (0.15 mL) was added and the reaction mixture was refluxed for 0.5 hour. Borane dimethyl sulfide complex (0.7 mL) was added and the reaction mixture was refluxed for 1 hour. The reaction mixture was cooled and methanol and isopropanolic HCl were added. This solution was refluxed for 0.5 hours and the solvents removed. The residue was chromatographed on silica gel eluting with 10% methanol-methylene chloride. Appropriate fractions were combined, isopropanolic HCl added and the solvents evaporated to give 110 mg (27%) of the title compound as its hydrochloride salt. Recrystallization from isopropanol afforded analytically pure material as the hydrochloride salt solvated with one equivalent of isopropanol.

$^1$H NMR (DMSO-d$_6$) δ: 1.06 (d, 6H, isopropanol), 1.29 (t, 3H), 3.12 (m, 2H), 3.80 (m, 2H), 4.20 (m, 2H), 4.67 (m, 2H), 7.86 (s, 1H), 8.20 (br s, 2H).

EXAMPLE 3

4-Isobutyl-7-sulfamoyl-2,3,4,5-tetrahydrothieno[3,2-f]-1,4-thiazepine-1,1-dioxide Following the procedure described in Example 2 but replacing the acetic anhydride with isobutyryl chloride, the title compound was obtained as its hydrochloride salt solvated with isopropanol in a two-step 32% overall yield, mp 160° C. (dec.).

Anal. calcd. for C$_{11}$H$_{18}$N$_2$O$_4$S$_3$•HCl•C$_3$H$_8$O: C, 38.65; H, 6.26; N, 6.44. Found: C, 38.30; H, 6.60; N, 6.34.

The title compound is obtained more directly as the free base following the procedure described in Example 8 infra in 45% yield, after crystallization from ethyl acetate-n-butyl chloride, mp 149°–151° C.

$^1$H NMR (CDCl$_3$/DMSO-d$_6$) δ: 0.87 (d, 3H, J-7.2 Hz), 1.70 (m, 1H), 2.13 (d, 2H, J-7.8 Hz), 3.34 (m, 2H), 3.64 (m, 2H), 4.10 (s, 2H), 7.21 (br s, 2H), 7.40 (s, 1H).

Anal. calcd for C$_{11}$H$_{18}$N$_2$O$_4$S$_3$•¼ n-butylchloride: C, 39.85; H, 5.64; N, 7.75. Found: C, 39.53; H, 5.41; N, 7.69.

EXAMPLE 4

Step A: Preparation of 3(R,S)-methyl-7-sulfamoyl-3,4-dihydrothieno[3,2-f]-1,4-thiazepin-5(2H)-one To a mixture of potassium tert-butoxide (8.56 g, 0.076 mol) in ethanol (75 mL) was added 2(R,S)-aminopropanethiol (3.1 g, 0.0246 mol) and ethyl 2-chloro-5-sulfamoylthiophene-3-carboxylate (5.98 g, 0.022 mol). The mixture was heated at reflux for 24 hours, and then allowed to stand at room temperature for 24 hours. Following removal of most of the solvent by vacuum concentration, the mixture was acidified to pH 3 with dilute hydrochloric acid. The resulting solids were removed by filtration and dried to give 4.44 g of the title compound, mp 184°–187° C.

$^1$H NMR (DMSO-d$_6$) δ: 1.25 (d, J=6.6 Hz, 3H); 3.09 (t, J=11.4 Hz, 1H); 3.37 (dd, J=3, 11.4 Hz, 1H); 3.6–3.7 (m, 1H); 7.56 (s, 1H); 7.82 (s, 2H); 8.34 (d, J=5.7 Hz, 1H).

Anal. Calcd. for C$_8$H$_{10}$N$_2$O$_3$S$_3$: C, 34.52; H, 3.62; N, 10.06. Found: C, 34.69; H, 3.80; N, 9.83.

Step B: Preparation of 3(R,S)-methyl-7-sulfamoyl-3,4-dihydrothieno[3,2-f]-1,4-thiazepin-5(2H)-one-1,1-dioxide To a mixture of 3(R,S)-methyl-7-sulfamoyl-3,4-dihydrothieno[3,2-f]-1,4-thiazepin-5(2H)-one (4.30 g, 15.4 mmol), in methanol (50 mL), cooled in an ice bath, was added Oxone® (4.30 g, 15.4 mmol), in H$_2$O (5 mL). The mixture was allowed to warm to room temperature and then stirred for 4 hours. The solids were removed by filtration and washed with water. A second crop was obtained from the filtrate. A nearly quantitative yield of the title compound was obtained, mp 295°–300° C. (dec).

$^1$H NMR (CD$_3$CN) δ: 1.57 (d, J=6.9 Hz, 3H); 2.83 (m, 2H); 3.77 (dd, J=11.4, 13.5 Hz, 1H); 3.94 (dd, J=3.6, 13.5 Hz, 1H); 4.22–4.37 (m, 1H); 7.34 (s, 1H); 7.76 (s, 1H).

Anal calcd. for C$_8$H$_{10}$N$_2$O$_5$S$_3$:
C, 30.96; H, 3.25; N, 9.03.
Found: C, 31.15; H, 3.38; N, 8.85.

Step C: Preparation of 7-sulfamoyl-3(R,S)-methyl-2,3,4,5-tetrahydrothieno[3,2-f]-1,4-thiazepine-1,1-dioxide hydrochloride To a round bottomed flask were added THF (250 mL) along with 3-methyl-1,1-dioxide-7-sulfamoyl-3,4-dihydrothieno[3,2-f]-1,4-thiazepin-5(2H)-one (5.0 g, 16.1 mmole). To this suspension was added borane-tetrahydrofuran complex (53.9 mL, 53.9 mmole). The reaction was heated at reflux for four hours. Additional borane (59.9 mL, 53.9 mmole) was added and the mixture was heated at reflux an additional 8 hours. The reaction mixture was allowed to cool and stand over the weekend. Acetic acid (4.0 mL) was added and the reaction mixture was stirred for 2.0 hours. The solid material was collected, dissolved in sodium bicarbonate solution, extracted with ethyl acetate and dried (MgSO$_4$). Solvent removal yielded a white solid, 3.5 g (73%). The solvent was dissolved in isopropanol and ethanol/HCl added. A white solid precipitated yielded 3.05 g (76%) of the hydrochloride salt mp=270° C. (dec.).

$^1$H NMR (d$_6$-DMSO) δ: 1.44 (d, 3H, J-6.6 Hz), 3.30–4.15 (m, 3H), 4.29–4.71 (dd 2H), 7.84 (s, 1H), 8.20 (s, H$_2$NSO$_2$—).

Anal. Calcd. for C$_8$H$_{12}$N$_2$O$_4$S$_3$•HCl: C, 28.86; H, 3.94; N, 8.42. Found: C, 28.69; H, 4.32; N, 8.38.

EXAMPLE 5

7-sulfamoyl-4-ethyl-3(R,S)-methyl-2,3,4,5-tetrahydrothieno[3,2-f]-1,4-thiazepine-1,1-dioxide-maleate The filtrate from the initial work-up of Example 4, Step C, was concentrated. The residue was dissolved in sodium bicarbonate solution and extracted with ethyl acetate. The organic layer was dried (MgSO$_4$) and the solvent removed. Medium pressure chromatography (silica gel, methanol/chloroform, 10/90) followed by recrystallization (CH$_3$CN) with addition of maleic acid yielded the N-ethyl substituted maleate salt 389.0 mg (5%) mp=131°–135° C.

$^1$H NMR (d$_6$-DMSO) δ: 0.99 (t, 3H, J-6.9 Hz), 1.26 (d, 3H, J-5.7 Hz), 2.05–2.62 (m, -2H), 3.55 (q, 1H, J-6 Hz), 3.82 (m, 2H), 4.01–4.41 (dd, 2H), 6.24 (s, maleate), 7.68 (s, 1H), 8.04 (s, H$_2$NSO$_2$—).

Anal. Calcd for C$_{10}$H$_{16}$N$_2$O$_4$S$_3$•C$_4$H$_4$O$_4$•½ CH$_3$CN: C, 39.07; H, 4.70; N, 7.60. Found: C, 38.87; H, 4.56; N, 7.71.

EXAMPLE 6

7-Sulfamoyl-4-isobutyl-3(R,S)-methyl-2,3,4,5-tetrahydrothieno[3,2-f]-1,4-thiazepine-1,1-dioxide To a round bottomed flask were added dimethylformamide (20 mL) along with triethylamine (1.33 mL, 9.5 mmole), 7-sulfamoyl-3(R,S)-methyl-2,3,4,5-tetrahydrothieno[3,2-f]-1,4-thiazepine-1,1-dioxide (1.27 g, 3.8 mmole) and isobutylbromide (1.60 g, 11.4 mmole). The reaction mixture was heated at 80° C. for 24 hours. Additional alkylating reagent was added (0.75 g, 5.5 mmole) and the reaction mixture heated an additional 36 hours. The reaction mixture was poured onto water and the aqueous mixture acidified with HCl. The resulting mixture was washed with ethyl acetate, basified with sodium hydroxide and washed with methylene chloride. The pH was adjusted to 7.5 and the solution was extracted with ethyl acetate. The extract was dried (MgSO$_4$) and the solvent was removed to yield 460 mg of an oil. Medium pressure chromatography using silica with a chloroform mobile phase resulted in 150 mg (11%) of a solid mp=152°–154° C.

$^1$H NMR (CDCl$_3$) δ: 0.81 (d, 3H, J-6.6 Hz), 0.88 (d, 3H, J-6.6 Hz), 1.31 (d, 3H, J-7.0 Hz), 1.71 (m, 1H), 1.96 (m, 2H), 3.08 (dd, 1H, J-1.7, 15.4 Hz), 3.46 (dd, 1H, J-10.2, 14.9 Hz), 4.00 (t, 1H), 4.16 (s, 2H), 5.20 (br s, 2H, H2NSO$_2$—), 7.42 (S, 1H).

EXAMPLE 7

2(R,S)-Methyl-7-sulfamoyl-2,3,4,5-tetrahydrothieno[3,2-f]-1,4-thiazepine-1,1-dioxide hydrochloride

Step A: Preparation of 2(R,S)-methyl-7-sulfamoyl-3,4-dihydrothieno-[3,2-f]-1,4-thiazepin-5(2H)-one Following the procedure described in Example 1, Step E, 2-chloro-3-carboethoxythiophene-2-sulfonamide was reacted with 1-amino-2-propanethiol hydrochloride in the presence of four equivalents of sodium ethoxide to give, after recrystallization from ethyl acetate, a 51% yield of title compound, mp 199°–201° C.

$^1$H NMR (DMSO-d$_6$) δ: 1.27 (d, 3H, J-6.9 Hz), 3.09 (dt, 1H, J-9.0, 15.3 Hz), 3.42 (m, 1H), 3.85 (m, 1H), 7.57 (s, 1H), 7.83 (br s, 2H), 8.52 (br t, 1H).

Anal. calcd for C$_8$H$_{10}$N$_2$O$_3$S$_3$: C, 34.51; H, 3.62; N, 10.07. Found: C, 34.30; H, 3.36; N, 10.06.

Step B: Preparation of 2(R,S)-methyl-7-sulfamoyl-3,4-tetrahydrothieno-[3,2-f]-1,4-thiazepin-5(2H)-one-1,1-dioxide Following the procedure described in Example 1, Step F, 2(R,S)-methyl-7-sulfamoyl-3,4-dihydrothieno[3,2-f]-1,4-thiazepin-5(2H)-one was oxidized with Oxone® to give an 85% yield of title compound, mp 243°–245° C.

$^1$H NMR (DMSO-d$_6$) δ: 1.29 (d, 3H), J-6.9 Hz), 3.27 (m, 1H), 3.70 (m, 1H), 3.86 (m, 1H), 7.74 (s, 1H), 8.15 (br s, 2H), 8.71 (br t, 1H).

Anal. calcd for C$_8$H$_{10}$N$_2$O$_5$S$_3$:
C, 30.96; H, 3.25; N, 9.03. Found: C, 30.98; H, 3.15; N, 8.86.

Step C: Preparation of 2(R,S)-methyl-7-sulfamoyl-2,3,4,5-tetrahydrothieno[3,2-f]-1,4-thiazepine-1,1-dioxide hydrochloride Following the procedure described in Example 4, Step C, 2(R,S)-methyl-7-sulfamoyl-3,4-dihydrothieno[3,2-f]-1,4-thiazepine-5(2H)-one-1,1-dioxide was reduced with borane to give a 32% yield of the title compound as its hydrochloride salt, mp: 240°–242° C. dec.

$^1$H NMR (DMSO-$d_6$) δ: 1.25 (d, 3H, J-6.9 Hz), 3.20(dd, 1H, J-8.1, 8.1 Hz), 3.51 (m, 2H), 3.97 (q, 2H), J-15 Hz), 7.62 (s, 1H), 8.06 (br s, 2H).

Anal. calcd for $C_8H_{12}N_2O_4S_3 \cdot HCl$: C, 28.86; H, 3.94; N, 8.42. Found: C, 28.80; H, 4.25; N, 8.36.

Alternatively, if the initial quench of the reaction mixture with acetic acid is omitted, the yield of title compound is improved to 64%.

EXAMPLE 8

2(R,S)-Methyl-4-ethyl-7-sulfamoyl-2,3,4,5-tetrahydro-thieno[3,2-f]-1,4-thiazepine-1,1-dioxide maleate Following the procedure described in Example 5, the filtrate from Example 7, Step C, was worked up to obtain a 17% yield of the title compound as its maleate salt, mp 158°–160° C.

$^1$H NMR (DMSO-$d_6$) δ: 1.01 (t, 3H, J-7.5 Hz), 1.23 (d, 3H, J-6.9 Hz), 2.50 (m, H), 3.36 (d, 2H, J-5.4 Hz), 3.83 (q, 1H, J-6.0 Hz), 4.10 (q, 2H, J-15.3 Hz), 6.25 (s, 2H, maleate), 7.68 (s, 1H), 8.06 (br s, 2H).

Anal. calcd for $C_{10}H_{16}N_2O_4S_3 \cdot C_4H_4O_4$: C, 38.17; H, 4.58; N, 6.36. Found: C, 38.05; H, 4.91; N, 6.47.

EXAMPLE 9

2(R,S)-Methyl-4-isobutyl-7-sulfamoyl-2,3,4,5-tetrahydrothieno[3,2-f]-1,4-thiazepine-1,1-dioxide A solution of 2(R,S)-methyl-7-sulfamoyl-2,3,4,5-tetrahydrothieno[3,2-f]-1,4-thiazepin-1,1-dioxide (1.18 g, 4.0 mmol) in dry dimethylformamide (6 mL) containing isobutylbromide (1.3 mL, 12 mmol) and triethylamine (2.3 mL, 16 mmol) was warmed at 80° C. for 20 hours in a sealed tube. The reaction mixture was poured into water and the product extracted into ethyl acetate. This extract was dried ($Na_2SO_4$), filtered and evaporated. The residue was chromatographed on silica gel and eluted with a 0–1% methanol/chloroform gradient to give 900 mg (64%) of title compound which slowly crystallized. Recrystallization from methylene chloride/butyl chloride gave analytically pure material, mp 158°–159.5° C.

$^1$H NMR (acetone-$d_6$)δ: 0.85 (dd, 6H, J-6.6, 9.6 Hz), 1.29 (d, 3H, J-9.6 Hz), 1.80 (m, 1H), 2.24 (d, 2H, J-7.2 Hz), 3.36 (dd, 1H, J-2.4, 15.3 Hz), 3.47 (dd, 1H, J-9.3, 15.3 Hz), 3.71 (m, 1H), 4.10 (q, 2H, J-15.6 Hz), 7.20 (br s, 2H), 2.61 (s, 1H).

Anal. calcd for $C_{12}H_{20}N_2O_4S_2$: C, 40.89; H, 5.72; N, 7.95. Found: C, 40.94; H, 5.87; N, 7.97.

EXAMPLE 10

5(R,S)-Methyl-7-sulfamoyl-2,3,4,5-tetrahydrothieno-[3,2-f]-1,4-thiazepine-1,1-dioxide hydrochloride Step A: Preparation of N-methyl-N-methoxy-2-chloro-5-sulfamoylthiophene-3-carboxamide 1,1-Carbonyldiimidazole (7.70 g, 0.047 mol) was added portionwise to a solution of 5-chloro-4-carboxy-thiophene-2-sulfonamide (7.25 g, 0.03 mol) in DMF (60 mL). After two hours, N-methylpiperidine (6.0 mL, 0.05 mol) and N,O-dimethylhydroxylamine hydrochloride (5.2 g, 0.05 mol) were added to the reaction mixture. After an additional four hours at room temperature, the reaction mixture was poured into ice/water saturated with $NaHCO_3$. The crude product was extracted into ethyl acetate, the extract was dried (anhydrous $Na_2SO_4$), filtered and evaporated. The crude residue was chromatographed on silica gel and eluted with 59% methanol/methylene chloride to give 3.45 g (40%) of white solid product, mp 223°–225° C.

$^1$H NMR (DMSO-$d_6$) δ: 3.26 (s, 3H), 3.58 (s, 3H), 7.56 (s, 1H), 7.94 (s, 2H).

Step B: Preparation of 4-acetyl-5-chlorothiophene-2-sulfonamide

A solution of 1.5M methyllithium/ether (26 mL, 0.039 mol) was added dropwise to a solution of N-methyl-N-methoxy-2-chloro-5-sulfamoylthiophene-3-carboxamide (3.25 g, 0.011 mol) in dry THF (145 mL) under a nitrogen atmosphere, cooled to −78° C. After two hours, the reaction mixture was poured carefully into ice/dil. HCl and the product was extracted into ethyl acetate. This extract was washed with water and brine, dried ($Na_2SO_4$), filtered and evaporated to give 2.82 g of crude solid product. This material was chromatographed on silica gel and eluted with 40% ethyl acetate/hexane to give 1.7 g (74%) of product. Recrystallization from ethyl acetate/hexane gave 1.68 g of product, mp 128°–130° C.

$^1$H NMR (DMSO-$d_6$) δ: 2.57 (s, 3H), 7.82 (s, 1H), 7.96 (s, 2H).

Anal. calcd for $C_6H_6ClO_3S_2$: C, 30.06; H, 2.52; N, 5.84. Found: C, 30.14; H, 2.63; N, 5.60.

Step C: Preparation of 5(R,S)-methyl-7-sulfamoyl-2,3,4,5-tetrahydrothieno[3,2-f]-1,4-thiazepine Sodium metal (0.46 g, 0.02 mol) was dissolved in absolute ethanol (50 mL), under a nitrogen atmosphere and 2-mercaptoethylamine (1.55 g, 0.02 mol) was added. After 10 minutes, 4-acetyl-5-chlorothiophene-2-sulfonamide (1.63 g, 0.007 mol) in dry ethanol (70 mL) was added to the reaction and the mixture refluxed for 18 hours. The reaction was cooled to room temperature and sodium borohydride (1.0 g, 0.026 mol) was added. After three hours the reaction mixture was poured into ice water and acidified with 6N HCl. The aqueous solution was extracted with ethyl acetate and the aqueous solution made basic with $NaHCO_3$ and $Na_2CO_3$. The product was extracted into ethyl acetate, the extract was dried ($Na_2SO_4$), filtered and evaporated. The residue (1.77 g) was crystallized from ethyl acetate-methanol to give analytically pure product (1.58 g, 85%), mp 182°–185° C.

$^1$H NMR (DMSO-$d_6$) δ: 1.41 (d, 3H, J-7.2 Hz), 2.61 (m, 1H), 2.19 (m, 1H), 3.14 (m, 1H), 3.48 (m, 1H), 3.90 (q, H, J-7.2 Hz), 7.35 (s, 1H), 7.64 (br s, 2H).

Anal. calcd for $C_8H_{12}N_2O_2S_3$: C, 36.34; H, 4.57; N, 10.60. Found: C, 36.12; H, 4.66; N, 10.65.

Step D: Preparation of 4-isobutyryl-5(R,S)-methyl-7-sulfamoyl-2,3,4,5-tetrahydrothieno[3,2-f]-1.4-thiazepine To a partial suspension of 5(R,S)-methyl-2-sulfamoyl-2,3,4,5-tetrahydrothieno[3,2-f]-1,4-thiazepine (900 mg, 3.4 mmol) in tetrahydrofuran (25 mL) was added isobutyryl chloride (0.36 mL, 3.4 mmol) followed by triethylamine (0.48 mL, 3.4 mmol). This mixture was stirred at ambient temperature for several hours and then poured into water containing dilute HCl. The product was extracted into ethyl acetate, the extract washed with $NaHCO_3$ solution and then dried and the solvent evaporated. Trituration of the residue with diethyl ether containing some methylene chloride yielded 960 mg (95%) of crystalline title compound, mp 181°–183° C., as a 2:1 mixture of rotamers.

Anal. calcd for $C_{12}H_{18}N_2O_3S_3$: C, 43.09; H, 5.44; N, 8.38. Found: C, 43.29; H, 5.47; N, 8.29.

Step E: Preparation of 4-isobutyryl-5(R,S)-methyl-7-sulfamoyl-2,3,4,5-tetrahydrothieno[3,2-f]-1,4-thiazepine-1,1-dioxide To a solution of Oxone® (512 mg, 8.23 mmol) in water (30 mL) was added 4-isobutyryl-5(R,S)-methyl-7-sulfamoyl-2,3,4,5-tetrahydrothieno[3,2-f]-1,4-thiazepine (1.48 g, 4.43 mmol) and methanol (5 mL). The suspension was warmed at 60° C. for three hours as a clear solution formed and then an oily precipitate was formed. The product was extracted into ethyl acetate. The extract was dried ($Na_2SO_4$) and filtered through a pad of charcoal and then the solvent was evaporated. The residue was triturated with diethyl ether to give an amorphorus white solid product (1.56 g, 95%) which remained a mixture of rotamers.

Step F: Preparation of 5(R,S)-methyl-7-sulfamoyl-2,3,4,5-tetrahydrothieno[3,2-f]-1,4-thiazepine-1,1-dioxide hydrochloride A suspension of 4-isobutyryl-5(R,S)-methyl-7-sulfamoyl-2,3,4,5-tetrahydrothieno[3,2-f]-1,4-thiazepine-1,1-dioxide (500 mg, 1.5 mmol) in water (8 mL) and concentrated HCl (4 mL) containing ethanol (3 mL) was warmed at 100° C. for 2 days. The cooled solution was made weakly basic with $NaHCO_3$ and the product was extracted into ethyl acetate. The extract was dried ($Na_2SO_4$), filtered through a pad of charcoal and the solvent evaporated. Trituration of this residue afforded 361 mg (80%) of title compound, mp 236°–238° C. dec.

$^1H$ NMR (Acetone-$d_6$) δ: 1.53 (d, 3H, J-6.9 Hz), 3.44 (complex of 2H), 3.55 (m, 2H), 4.24 (q, 1H, J-6.9 Hz), 7.53 (br s, 2H), 7.57 (s, 1H).

This free base was suspended in methanol and treated with ethanolic HCl. This mixture was concentrated to dryness. The residue was dissolved in isopropanol and methylene chloride and allowed to stand as the hydrochloride salt slowly crystallized out in 80% yield, mp 257°–259° C.

Anal. calcd for $C_8H_{12}N_2O_4S_3\cdot HCl$: C, 28.86; H, 3.94; N, 8.42. Found: C, 29.06; H, 3.86; N, 8.43.

EXAMPLE 11

4-Isobutyl-5(R,S)-methyl-7-sulfamoyl-2,3,4,5-tetrahydrothieno[3,2-f]-1,4-thiazepine-1,1-dioxide To a solution of 4-isobutyryl-5(R,S)-methyl-7-sulfamoyl-2,3,4,5-tetrahydrothieno[3.2-f]-1,4-thiazepine-1,1-dioxide (1.009 g, 2.75 mmol) in dry tetrahydrofuran (30 mL), under an inert atmosphere was added 1M borane•THF (9 mL, 9.0 mmol) and the reaction mixture was refluxed for three hours. Concentrated HCl and water were then added to the cooled reaction mixture. After refluxing this mixture for 0.5 hours, the solvent was removed, the residue was made basic with $NaHCO_3$ and the product was extracted into ethyl acetate. The extract was dried ($Na_2SO_4$), filtered and the solvent evaporated. Trituration of the residue with diethyl ether and n-butyl chloride gave 637 mg (65%) of crystalline product. Recrystallization of the solid from diethyl ether twice afforded analytically pure title compound (446 mg), mp 125°–127° C.

$^1H$ NMR (Acetone-$d_6$) δ: 0.81 (d, 3H, J-6.6 Hz), 0.88 (d, 3H, J-6.6 Hz), 1.57 (d, 3H, J-7.2 Hz), 1.76 (m, 1H), 2.13 (m, 2H), 3.36 (m, 1H), 3.60 (m, 2H), 3.74 (m, 1H), 4.50 (q, 1H, J-7.2 Hz), 7.17 (br s, 2H), 7.57 (s, 1H).

Anal. calcd for $C_{12}H_{20}N_2O_4S_3$: C, 40.89; H, 5.72; N, 7.95. Found: C, 41.06; H, 5.79; N, 7.72.

EXAMPLE 12

| Ophthalmological Formulation | | |
|---|---|---|
| Novel Compound | 1 mg | 15 mg |
| Monobasic sodium phosphate $2H_2O$ | 9.38 mg | 6.10 mg |
| Dibasic sodium phosphate .$12H_2O$ | 28.48 mg | 16.80 mg |
| Benzalkonium chloride | 0.10 mg | 0.10 mg |
| Water for injection q.s. and | 1.0 ml | 1.0 ml |

The novel compound, phosphate buffer salts, and benzalkonium chloride are added to and dissolved in water. The pH of the composition is adjusted to 6.8 and diluted to volume. The composition is rendered sterile by ionizing radiation.

EXAMPLE 13

| Ophthalmological Formulation | |
|---|---|
| Novel Compound | 5 mg |
| Petrolatum q.s. and. | 1 gram |

The compound and the petrolatum are aseptically combined.

What is claimed is:

1. A compound of structural formula:

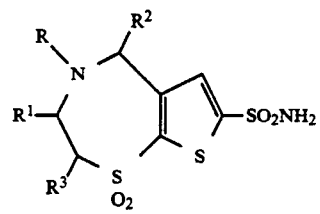

or the diastereomers the individual enantiomers, a mixture of the enantiomers, or an ophthalmologically acceptable salt of the compound, wherein R, $R^1$ and $R^2$ are independently hydrogen, $C_{1-5}$ alkyl or $C_{3-7}$ cycloalkyl; and $R^3$ is hydrogen or $C_{1-5}$ alkyl either unsubstituted or substituted with $C_{1-3}$ alkoxy, $C_{1-3}$ alkoxy-$C_{1-3}$ alkoxy, hydroxy, hydroxy-$C_{1-3}$ alkoxy or —$N(R^4)_2$ wherein the $R^4$ groups are the same or different and are hydrogen or $C_{1-3}$ alkyl.

2. The compound of claim 1 wherein $R^2$ is H.

3. The compound of claim 2, wherein R and $R^1$ are independently hydrogen or $C_{1-5}$ alkyl; and $R^3$ is hydrogen, $C_{1-5}$ alkyl or $C_{1-3}$ alkoxy-$C_{1-5}$ alkyl.

4. The compound of claim 3 which is:
7-Sulfamoyl-2,3,4,5-tetrahydrothieno[3,2-f]-1,4-thiazepine-1,1-dioxide;
4-ethyl-7-sulfamoyl-2,3,4,5-tetrahydrothieno-[3,2-f]-1,4-thiazepine-1,1-dioxide;
4-isobutyl-7-sulfamoyl-2,3,4,5-tetrahydrothieno[-3,2-f]-1,4-thiazepine-1,1-dioxide;
3(R,S)-methyl-7-sulfamoyl-2,3,4,5-tetrahydrothieno[3,2-f]-1,4-thiazepine-1,1-dioxide;
4-ethyl-3(R,S)-methyl-7-sulfamoyl-2,3,4,5-tetrahydrothieno[3,2-f]-1,4-thiazepine-1,1-dioxide;

4-isobutyl-3(R,S)-methyl-7-sulfamoyl-2,3,4,5-tetrahydrothieno[3,2-f]-1,4-thiazepine-1,1-dioxide;

2(R,S)-methyl-7-sulfamoyl-2,3,4,5-tetrahydrothieno[3,2-f]-1,4-thiazepine-1,1-dioxide;

4-ethyl-2(R,S)-methyl-7-sulfamoyl-2,3,4,5-tetrahydrothieno[3,2-f]-1,4-thiazepine-1,1-dioxide;

4-isobutyl-2(R,S)-methyl-7-sulfamoyl-2,3,4,5-tetrahydrothieno[3,2-f]-1,4-thiazepin-1,1-dioxide;

5(R,S)-methyl-7-sulfamoyl-2,3,4,5-tetrahydrothieno[3,2-f]-1,4-thiazepine-1,1-dioxide; or 4-isobutyl-5(R,S)-methyl-7-sulfamoyl-2,3,4,5-tetrahydrothieno[3,2-f]-1,4-thiazepin-1,1-dioxide.

5. An ophthalmic formulation comprising an ophthalmologically acceptable carrier and an effective amount of a compound of claim 1.

6. A method of treating ocular hypertension and glaucoma which comprises the topical administration to a patient in need of such treatment of an effective amount of the compound of claim 1.

* * * * *